United States Patent [19]

Schofield

[11] Patent Number: 4,877,732
[45] Date of Patent: Oct. 31, 1989

[54] BIOCHEMICAL PROCESS FOR THE PREPARATION OF NEW ORGANOFLUORINE COMPOUNDS

[75] Inventor: John A. Schofield, Kent, England

[73] Assignee: Shell Oil Company, Houston, Tex.

[21] Appl. No.: 69,137

[22] Filed: Jul. 2, 1987

[30] Foreign Application Priority Data

Jul. 8, 1986 [GB] United Kingdom ............... 8616614

[51] Int. Cl.$^4$ ........................... C12P 7/22; C12R 1/40
[52] U.S. Cl. .................................. 435/155; 435/156; 435/253.3; 435/877
[58] Field of Search .................. 435/155, 156, 253.3, 435/877, 155, 156

[56] References Cited

U.S. PATENT DOCUMENTS

| 4,508,822 | 4/1985 | Taylor | 435/155 |
| 4,532,209 | 7/1985 | Hagedorn | 435/156 |
| 4,535,059 | 8/1985 | Hsieh et al. | 435/142 |
| 4,634,668 | 1/1987 | Hagedorn | 435/146 |

FOREIGN PATENT DOCUMENTS 76606 4/1983 European Pat. Off. .

OTHER PUBLICATIONS

De Frank and Ribbons, *Biochem. & Biophys. Res. Comm.*, 70 (4) 1976, pp. 1129–1135.
Gibson et al., *Biochemistry*, 7 (7), 1968, p. 2653.
Gibson et al., *Biochemistry*, 9 (7), 1970, p. 1631.
Gibson et al., *Biochemistry*, 7 (11), 1978, p. 3795.

*Primary Examiner*—Herbert J. Lilling

[57] ABSTRACT

Novel compound cis-1,2-dihydroxy-3-trifluoromethyl-cyclohexa-3,5-diene (and certain fluoro-substituted analogues) can be produced biochemically by culturing a wild type or mutant strain of *P.putida* with benzotrifluoride or certain fluoro-substituted analogues as substrate.

5 Claims, No Drawings

BIOCHEMICAL PROCESS FOR THE PREPARATION OF NEW ORGANOFLUORINE COMPOUNDS

This invention relates to certain novel organofluorine compounds and to their preparation by a biochemical process.

Defrank and Ribbons (Biochem. & Biophys. Res. Comm., 70, 4, 1976, p. 1129–1135), while investigating the p-cymene pathway in certain strains of the microorganism *Pseudomonas putida*, employed as a model compound 4-trifluoromethyl benzoic acid as a substrate for certain blocked mutants of *P. putida*. They found spectroscopic evidence for the accumulation of a diene diol which was readily subject to acid hydroylsis to yield 3-hydroxy-4-trifluoromethyl benzoic acid. The authors were primarily interested in throwing light on the metabolism of p-cymene via p-cumate.

In addition, the ability of the microorganism *Pseudomonas putida* to metabolise benzene and certain substituted benzenes to their corresponding catechols and further degradation products is known from the work of Gibson et al, Biochemistry, 7(7), 1968, p. 2653; and Biochemistry, 9(7), 1970, p. 1631. Thus, the metabolism is believed to follow the following enzyme catalysed reaction sequence:

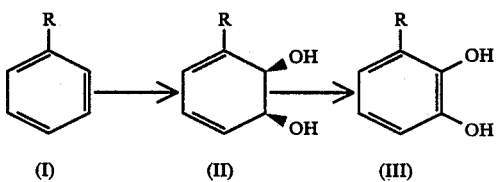

(I)  (II)  (III)

In accordance with this metabolic pathway, benzene (I; R=H), is converted by a dioxygenase to cis-1,2-dihydroxycyclohexa-3,5-diene (II; R=H) (sometimes known as "cis-benzene glycol" or "benzene dihydrodiol") which under the action of a diol dehydrogenase is converted to catechol (III; R=H), which is further enzymatically converted to further degradation products. A related pathway, where R is methyl, is believed to occur for toluene metabolism using *Pseudomonas putida* (Gibson et al, Biochemistry, 9(7), 1970, p. 1627).

While compounds of formulae (II) and (III) would be useful products, it has been found difficult to control the reaction to give sufficient yield of the desired compound as a pure product and both induction and mutation procedures have been used in attempts to give maximum yields of desired products. Thus attempts to produce a compound of formula (II) from strains of *P. putida* have relied on the need to induce the required enzymes for the conversion reactions using benzene or toluene as carbon source. Thus Gibson et al (Biochemistry 7(11), 1978, p. 3795) used toluene as carbon source when carrying out investigations on the ability of *P. putida* to oxidise halogenated benzenes, while Taylor (European Pat. No. 0076606) likewise employed toluene to induce the required enzymes in his preparation of compounds of formula (II) from mutant strains of *P. putida*.

The need to induce the required enzymes is a disadvantage from the point of view of commercialisation of such a biochemical process, as the introduction of another carbon source for induction purposes contaminates the reaction mixture and leads to problems in separating the compounds produced.

We have surprisingly found that certain substituted benzenes containing fluorine are converted by certain strains of *P. putida* to produce novel diene cis-diol compounds which are resistant to further reaction to form catechols and further breakdown products.

According to this invention we provide a compound of formula:

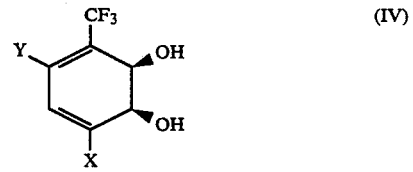

where each of X and Y independently is hydrogen or fluorine. Preferably X is hydrogen, and preferably Y is hydrogen.

According to a further aspect of this invention we provide a biochemical process for the preparation of a compound of formula (IV) from a compound of formula (V)

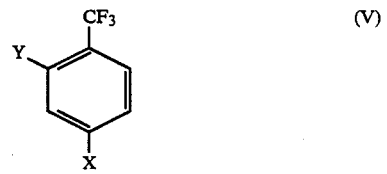

where each of X and Y independently is hydrogen or fluorine, comprising culturing a wild type *P. putida* microorganism as defined below, or a mutant thereof, supplying a compound of formula (V) to the culture in a suitable medium and subsequently recovering a compound of formula (IV) therefrom.

The *P. putida* referred to above is that deposited with effect from 6th Dec. 1985 with the National Collection of Industrial Bacteria, Torry Research Station, Aberdeen, Scotland and assigned the numerical designation NCIB 12190 and referred to herein as "*P. putida* NCIB 12190". *P. putida* NCIB 12190 and mutants thereof are described and claimed in our co-pending application Ser. No. 068,493, filed July 1, 1987. *P. putida* NCIB 12190 and certain mutants thereof are constitutive of the dioxygenase required for the process.

*P. putida* NCIB 12190 was isolated from a soil sample taken from ground within the Shell Refinery at Pernis, Rotterdam.

Suitable mutants are those obtained using chemical mutagenesis (such as by use of N-methyl-N'-nitro-N-nitrosoguanidine, referred to hereinafter as "NTG") or physical mutagenesis (using ultraviolet radiation).

The culture of *P. putida* or the mutant strain may be initially grown in the presence of any suitable carbon source. However, a preferred carbon source is succinic acid, suitably in the form of a salt such as disodium succinate. Other similar, but less expensive, carbon sources are those derived from citric acid and fumaric acid, e.g. trisodium citrate and disodium fumarate.

An alternative preferred carbon source has been shown to be molasses, both in the form of sugar cane molasses, commercially available as "black strap molasses", and in the form of sugar beet molasses.

The medium employed is selected to optimise the yield of the compound of formula (IV). However, the medium preferably includes salts of succinic, citric or fumaric acid or molasses, as described above for the initial carbon source.

The product compound may be recovered from the resulting fermentation broth by any suitable means, such as adsorption onto granulated charcoal, followed by stripping with a suitable solvent with further purification as necessary dependent on the intended use of the product. Alternative recovery means include solvent extraction.

In view of the above referenced work by Gibson et al and other workers which show that *P. putida* microorganisms can live on benzene or toluene and catalyse the entire metabolic pathway to muconic acids and further breakdown products, it is particularly surprising to find that compounds of formula (V) give, as sole products, compounds of formula (IV) when used as substrates for strains of *P. putida*. It thus appears that compounds of formula (IV) cannot act as substrates for the diol dehydrogenase of *P. putida*, which enzyme is required to catalyse the next step (II to III) in the overall reaction sequence described above. This selectivity in the case of compounds (IV) and (V) where X is fluorine is particularly surprising as the p-chloro-benzotrifluoride is not a suitable substrate for the reaction and no substantial conversion to the corresponding diol has been observed.

The compounds of formula (IV) are valuable new intermediates, for example in the fields of polymers, pharmaceuticals and organo-fluorine agrochemicals. The presence of the trifluoromethyl substituent often conveys uniquely interesting biological properties. Thus for example, cis-1,2-dihydroxy-3-trifluoromethyl-cyclohexa-3,5-diene (IV; X=H, Y=H) can be converted chemically into a wide range of trifluoromethyl aromatics, aliphatics and alicyclics. Examples are its dehydration to o- and m-trifluoromethylphenol, both valuable intermediates. Thus, o-trifluoromethylphenol can be used in the preparation of polymers which form blocking resistant films, in the preparation of certain anti-inflammatory drugs and as calcium fluoride depressants in compositions for froth flotation of zinc sulphide. m-Trifluoromethylphenol is useful in the preparation of certain phenylacetic esters which lower the levels of blood cholesterol and triglycerides, in the preparation of certain peptides and plant protective agents and in the preparation of certain soluble copper phthalocyanine dyes.

*Pseudomonas putida* NCIB 12190 has been characterised and identified by the NCIB as follows:

Tests were at 25° C. and growth was on LAB M Nutrient Agar unless otherwise stated.

Cell Morphology

After growth for 24 hours at 30° C. on succinate agar, and transfer to Nutrient broth +0.75%w agar, by phase contrast at ×630 magnification the cells are small short rods or cocci in clusters.

Gram negative
Spores −
Motility +
Colonial Morphology

After 48 hours growth, colonies are round, regular, entire, smooth, opaque, low convex, off-white and less than 1 mm in diameter.

Growth on Glucose Peptone Water Sugars
37° C. +
41° C. −
Catalase +
Oxidase, Kovacs +
O-F glucose Oxidative "O-F glucose" was performed using the oxidation-fermentation medium of Hayward and Hodgkiss, J. Gen. Microbiol. 26 (1961) 133–140, supplemented with 1%w filter-sterilised D-glucose. A tube sample was inoculated and incubated for 14 days.

*Pseudomonas putida* NCIB 12190 can conveniently be stored on nutrient agar slopes at 4° C., or as a freeze-dried material.

The UV mutant of *Pseudomonas putida* NCIB 12190 described in Example 1 had the same characteristics as those described above, with the exception of motility-negative.

The following examples illustrate the invention.

EXAMPLE 1

Preparation of cis-1,2-dihydroxy-3-trifluoromethyl-cyclohexa-3,5-diene using a mutant of *P. putida* NCIB 12190

(a) Nutrient solution
Yeast extract: 3 g
Disodium succinate.6H$_2$O: 10 g
(NH$_4$)$_2$SO$_4$: 2 g
Metals solution: 10 ml
25 mM Phosphate buffer, pH 7.0: 1000 ml (b) Metals solution
CaCl$_2$.2H$_2$O: 125 mg
MnSO$_4$.4H$_2$O: 25 mg
ZnSO$_4$.7H$_2$O: 25 mg
Water: 100 ml (c) Peptone solution
MgSo.7H$_2$O: 2 g
Bactopeptone (Difco): 0.2 g
Water: 10 ml (d) Isolation of *P. putida* mutant Aliquots of 1 ml of a suspension of *P. putida* NCIB 12190 in phosphate buffer pH 7 were spread onto nutrient agar plates. The plates were irradiated using a chromatolux u.v. lamp for 5 to 30 minutes. The plates were incubated at 30° C. overnight and then placed in an atmosphere of fluorobenzene at 30° C. and incubated for a further 24 hours. 34 surviving colonies were purified and tested for their ability to accumulate fluorocatechol in shake flask experiments. Fluorocatechol was assayed by gas chromatography. In comparative experiments, one mutant strain accumulated 0.56 g/l in 3–4 hr. Under the same conditions the wild strain NCIB 12190 accumulated 0.41 g/l.

Peptone solution ((0.1 ml) was added to nutrient solution (50 ml) in a 250 ml conical flask, which was then inoculated with the mutant of *P. putida* isolated as described above and incubated at 30° C. on a shaker for 17 hours. Benzotrifluoride (0.1 ml) was added to the flask which was then sealed. After 6 hours incubation at 30° C. the concentration of cis-1,2-dihydroxy-3-trifluoromethyl-cyclohexa-3,5-diene (as shown by GLC) had reached 0.83 g/liter and the reaction was quenched by freezing. The product was isolated by saturation of the broth with sodium chloride and extraction with ether. Evaporation of the ether extract yielded material which was recrystallised from ether-pentane to give the diene-diol (IV; Y=H, X=H), m.p. 95°–97° C.

Calc for C$_7$H$_7$O$_2$F$_3$: C, 46.7; H, 3.9%
Found: C, 46.4; H, 4.0%

Circular dichroism maxima
(H₂O, 20°): Δε −2.2 (258 nm), −7.9 (216 nm)
Mass Spectrum
m/e 180 (M+)
U V spectrum
(H₂O): λmax 263 nm (ε4211)
¹H-NMR:
4.30(d, 1, CH(OH)), 4.52(d, 1, CH(OH), 6.05(m, 1, =CH—)) 6.09 (part of AB, 1, =CH—), 6.57 (m, 1, =CH—))
6.09(part of AB, 1, =CH—), 6.57(m, 1, =CH—)

EXAMPLE 2

Comparison of Benzotrifluoride and Fluorobenzene as substrates for *P. putida* NCIB 12190

Peptone solution described as in Example 1 (0.1 ml) was added to each of two aliquots (50 ml) of nutrient solution (as described in Example 1) contained in 250 ml conical flasks. Each flask was then inoculated with *P. putida* NCIB 12190 and incubated at 30° C. on a shaker for 17 hours.

Fluorobenzene (0.1 ml) (as comparison) and benzotrifluoride (0.1 ml) (in accordance with the invention) were added to flasks A and B respectively which were then sealed and further incubated at 30° C. on a shaker. The courses of the reactions were followed by GLC and the results are shown below. For flask A the yields of a compound of formula (II) (R=F) referred to below as "diene-diol") and a compound of formula (III) (R=F) (referred to below as "catechol") were determined. For flask B, the yields of the corresponding diene-diol compound (formula IV: Y=H, X=H) and the corresponding "catechol" (formula III: R=CF₃) were determined.

| | Flask A | |
|---|---|---|
| t(min) | Diol (II, R = F) Conc (mg/liter) | Catechol (III, R = F) Conc (mg/liter) |
| 43 | 41 | 45 |
| 126 | 27 | 155 |
| 262 | 0 | 150 |
| 435 | 0 | 53 |
| 1453 | 0 | 0 |

| | Flask B | |
|---|---|---|
| t(min) | Diol (IV, X=H, Y=H) Conc (mg/liter) | Catechol (III R=CF₃) Conc (mg/liter) |
| 54 | 219 | 0 |
| 135 | 302 | 0 |
| 272 | 434 | 0 |
| 444 | 444 | 0 |
| 1465 | 468 | 0 |

The results show clearly that whereas *P. putida* NCIB 12190 catalyses the conversion of fluorobenzene to 3-fluoro catechol (III; R=F) via cis-1,2-dihydroxy-3 fluorocyclohexa-3,5-diene (II; R=F), and one observes the formation and decay of the diene-diol and catechol as consecutive reactions, in the case of benzotrifluoride the reaction stops at the "diol" stage (IV; X=H, Y=H) and no corresponding catechol (III; R=CF₃) is formed.

EXAMPLE 3

Preparation of cis-1,2-dihydroxy-3-trifluoromethylcyclohexa-3,5-diene using *P. putida* NCIB 12190 and various carbon sources Nutrient Solution
Yeast extract: 3.0 g
(NH₄)₂SO₄: 2.0 g
Metals solution: 10 ml
Peptone solution: 2 ml
Carbon source: see Table 1 below
25 mM Phosphate buffer (pH 7): 1000 ml
Peptone solution: as used in Example 1
Metals solution: as used in Example 1.

Aliquots (50 ml) of nutrient solution containing added carbon source as shown in Table 2 were inoculated with *Pseudomonas putida* NCIB 12190 and incubated in 250 ml conical flasks on a shaker for 17 hours at 30° C. Benzotrifluoride (0.1 ml) was added to each flask which was tne sealed and further incubated on a shaker at 30° C.

Formation of product cis-1,2-dihydroxy-3-trifluoromethylcyclohexa-3,5-diene (IV; X=H, Y=H) was monitored by GLC and the results are given in Table 1.

TABLE 1

| Run | Carbon Source | Carbon Conc. (g/l) | Dry Cell Wt. (g/l) | Final Diene-Diol Conc. (g/l) |
|---|---|---|---|---|
| A | Disodium Succinate .6H₂O (10 g/liter) | 1.8 | 2.16 | 0.50 |
| B | Trisodium Citrate .2H₂O (10 g/liter) | 2.4 | 2.22 | 0.55 |
| C | Disodium Fumarate (10 g/liter) | 3.0 | 2.20 | 0.56 |
| D | Ethanol (10 g/liter) | 5.2 | 1.94 | 0.03 |
| F | Sucrose (4.2 g/liter) | 1.8 | 1.24 | 0.12 |

It will be noted that although cell growth occured in all cases, the production of the desired diene-diol product was greatly improved when using as carbon source succinate, citrate or fumarate.

EXAMPLE 4

Preparation of cis-1,2-dihydroxy-3-trifluoromethylcyclohexa-3,5-diene in a fermenter using *P. putida* NCIB 12190

Yeast extract medium (YEM):
10 g/l disodium succinate.6H₂O
2 g/l (NH₄)SO₄
3 g/l yeast extract (Difco)
0.4 g/l MgSO₄.7H₂O
0.4 g/l Bactopeptone in 25 mM potassium phosphate buffer, final pH 7.0.

8 liters of YEM in a fermenter were inoculated with a 20 h shake culture of *P. putida* NCIB 12190 (stock slant derived from a shake culture grown on benzene) grown on the same medium (50 ml). The organism was grown at 500 rpm; 500 ml air/min for 20 h, with a continuous feed of concentrated nutrient (disodium succinate (320 g) and (NH₄)₂SO₄ (64 g) in 1 liter of 0.025M potassium phosphate buffer pH 7.2) at 40 ml/h, reach a dry cell weight of 2.8 g/l. The aeration was then increased (550 rpm; 750 ml air/min) for 1 hr giving an oxygen tension of 20–30% air-saturated. Benzotrifluoride was then added at 50 μl/min via an HPLC pump. Using these settings no product was found in the reaction mixture by GLC. It was thus concluded that the combination of low substrate solubility and high aeration was stripping substrate into the exhaust gas before a high enough concentration could be reached for the reaction to occur. To reduce this effect while still maintaining an adequate oxygen tension (>30%) the stirrer speed was raised to 650 rpm while aeration was reduced to 300 ml/min. 5 g of substrate was added batchwise while still maintaining a flow of 50 μl/min. Product formation commenced immediately as judged by GLC and reached-0.3 g/l after 60 min. Further additions of substrate (5 ml) were made at approximately 2 h intervals while maintaining the continuous addition (50 μl/min). The product concentration reached 1.25 g/l after approximately 6 h at which point the run was terminated. The product was adsorbed onto charcoal followed by stripping in a Soxhlet apparatus ($Et_2O$:MeOH 3:1). Evaporation of the solvent yielded about 60 ml of aqueous solution of trifluoromethylcyclohexa-3,5-diene which crystallised upon addition of a trace of NaCl. Recrystallisation from $Et_2O$:petrol 1:4 yielded approximately 12 g (=1.5 g/l) of pure trifluoromethylcyclohexa-3,5-diene.

EXAMPLE 5

Preparation of cis-1,2-dihydroxy-3-trifluoromethyl-6-fluorocyclohexa-3,5-diene (IV; X=F, Y=H) using *P. putida* NCIB 12190

Example 1 was repeated using as substrate p-fluorobenzotrifluoride (V; X=F, Y=H) and wild type *P. putida* NCIB 12190 as the microorganism. Evaporation of the ether extract give a highly crystalline product identified by mass spectrometry as cis-1,2-dihydroxy-3-trifluoromethyl-6-fluorocyclohexa-3,5-diene (IV; X=F, Y=H). The results of mass spectrometry are shown in Table 2 with a parent ion at m/e=198.

TABLE 2

| m/e | % of base peak | m/e | % of base peak |
|-----|----------------|-----|----------------|
| 47  | 46             | 101 | 100            |
| 51  | 57             | 132 | 48             |
| 57  | 50             | 152 | 37             |
| 75  | 43             | 198 | 24             |
| 83  | 80             |     |                |

EXAMPLE 6

Preparation of cis-1,2-dihydroxy-3-trifluoromethyl-4-fluorocyclohexa-3,5-diene (IV; X=H, Y=F)

Wild type *P. putida* NCIB 12190 was grown in 50 ml of potassium phosphate buffer, 25 mM ph 7.0, which contained $(NH_4)_2SO_4$ (2 g/l); $MgSO_4$ $7H_2O$ (0.4 g/l) $FeSO_4.7H_2O$ (0.04 g/l); Bactopeptone (0.04 g/l) and benzene (50 μl). The culture was incubated in a sealed flask at 30° on a shaker for 18 hours. The cells were collected by centrifuging and resuspended in 50 ml of potassium phosphate buffer (25 mM, pH 7.0). Ethanol (100 μl) and o-fluorobenzoltrifluoride (100 mg) were added to the resuspended cells in a 250 ml sealed flask. The mixture was allowed to react at 30° C. with shaking for 24 hours. The culture medium, after centrifugation, was extracted with ethyl acetate and the extract was dried over $Na_2SO_4$ and evaporated. The major component in the residue was shown to be cis-1,2-dihydroxy-4-fluoro-3-(trifluoromethyl)cyclohexa-3,5-diene by mass spectrometry and $^1$H-NMR analysis, and by acid-catalysed dehydration to 4-fluoro-3-(trifluoromethyl)-phenol. The mass spectrum is shown in Table 3. The 360 MHZ proton NMR spectrum (in $CDCl_3$) showed multiplets at δ 4.47, 4.60, 5.92 and 6.23 p.p.m., with couplings consistent with the structure. A portion of the residue was treated with 2M hydrochloric acid overnight, and the mixture was extracted with ethyl acetate. The major product in the extract was 4-fluoro-3-(trifluoromethyl)phenol, identified by comparison of the mass spectrum, $^1$H-NMR and $^{19}$F-NMR results with those for an authentic chemically synthesised sample.

TABLE 3

| m/e | % of base peak | m/e | % of base peak |
|-----|----------------|-----|----------------|
| 51  | 36             | 132 | 40             |
| 57  | 36             | 152 | 47             |
| 69  | 28             | 158 | 56             |
| 75  | 32             | 169 | 17             |
| 83  | 54             | 180 | 12             |
| 101 | 100            | 198 (M+) | 53         |
| 102 | 50             |     |                |

I claim:

1. A biochemical process for the preparation of a compound of formula (IV)

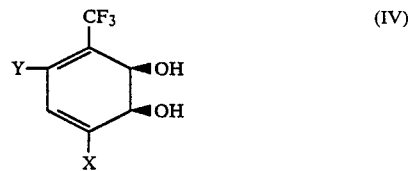

(IV)

from a compound of formula (V):

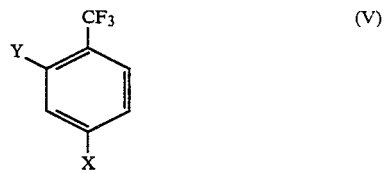

(V)

where each of X and Y independently is hydrogen or fluorine, comprising culturing a microorganism selected from *P. putida* NCIB 12190 and mutants thereof, supplying a compound of formula (V) to the culture in a suitable medium and subsequently recovering a compound of formula (IV) therefrom.

2. A process according to claim 1, wherein the microorganism is cultured in the presence of a salt of succinic, citric or fumaric acid.

3. A process according to claim 1 or 2, wherein the medium comprises a salt of succinic, citric or fumaric acid.

4. A process according to any one of claims 1 to 3 wherein the microorganism is wild type *P. putida* NCIB 12190.

5. A process according to any one of claims 1 to 3 wherein the microorganism is a UV mutant of *P. putida* NCIB 12190.

* * * * *